(12) United States Patent
Palfy et al.

(10) Patent No.: US 6,470,696 B1
(45) Date of Patent: Oct. 29, 2002

(54) DEVICES AND METHODS FOR SENSING CONDENSATION CONDITIONS AND FOR REMOVING CONDENSATION FROM SURFACES

(76) Inventors: Valerie Palfy, P.O. Box 11, Paoli, PA (US) 19301; Don A. Skomsky, 554 Highland Rd., West Chester, PA (US) 19380

(*) Notice: Subject to any disclaimer, the term of this patent is extended or adjusted under 35 U.S.C. 154(b) by 0 days.

(21) Appl. No.: 09/953,891

(22) Filed: Sep. 18, 2001

(51) Int. Cl.[7] .......................... F25D 21/02; G05D 23/00
(52) U.S. Cl. ................. 62/140; 62/3.4; 62/239; 62/150; 15/250.05; 219/203; 236/91 C
(58) Field of Search .................. 62/140, 3.4, 150, 62/239, 272; 15/250.05; 126/271.1; 219/507, 508, 509, 203, 494, 497; 236/91 C; 165/202, 222, 223

(56) References Cited

U.S. PATENT DOCUMENTS

| | | |
|---|---|---|
| 4,109,562 A | 8/1978 | MacDonald |
| 4,586,342 A | 5/1986 | Morishita et al. |
| 4,701,052 A | 10/1987 | Schoen, Jr. |
| 4,915,715 A | 4/1990 | Oshima et al. |
| 5,575,835 A | 11/1996 | Bailey et al. |
| 5,653,904 A | 8/1997 | Adlparvar et al. |
| 5,665,146 A | 9/1997 | Mizobe |
| 5,801,307 A | 9/1998 | Netzer |
| 5,809,826 A | 9/1998 | Baker, Jr. |
| 6,049,069 A | 4/2000 | Hochstein |
| 6,101,815 A | 5/2000 | Van Oort et al. |
| 6,112,807 A | 9/2000 | Dage |
| 6,205,805 B1 | 3/2001 | Takahashi et al. |
| 6,207,967 B1 | 3/2001 | Hochstein |
| 6,213,198 B1 | 4/2001 | Shikata et al. |
| 6,230,501 B1 | 5/2001 | Bailey, Sr. et al. |

OTHER PUBLICATIONS

Arnott, Ann; "The New High–Tech Gizmos"; Parade Magazine, 2001, p. 10.
Delphi Automotive Systems; "A Change in the Air: Intellek™ Humidity Sensor"; http:/www.delphiauto.com/news/solutions/monthly/ms420–03012001; 2001.
Iowa State Energy Center; "Input Devices and Sensors: Analog Devices"; http:/www.energy.iastate.edu/DDC_i%20o/chapter2io2.htm, pp. 6–8.
Linear Technology; "Choosing a Humidity Sensor"; Jul. 2001; wysiwyg://main.4/http://www.sensorsmag.com/articles/0701/54main.shtml.
Panametrics; "MiniCAP 2—Relative Humidity Sensor"; Feb. 2001.
Sensormag; "Sensors Wish List"; www.sensormag.com; May 2001.
Visteon Corporation; "Automotive OE"; http://www.visteon.com/technology/automative/cli_autodefog.html; 2001.
Xentaur; "High Capacitance, Quasi–Linear Response"; Jul. 2001, http://www.xentaur.com/HiCap.htm.
Xentaur; "Hyper–Thin–Film (HTF) $Al_2O_3$ Sensors"; Jul. 2001, http://www.xentaur.com/Hprthin.htm.

*Primary Examiner*—Chen-Wen Jiang
(74) *Attorney, Agent, or Firm*—Fish & Richardson P.C.

(57) ABSTRACT

In a device and method for sensing condensation conditions and for removing such condensation from a surface, a first thermal sensor is in thermally conductive contact with the surface. A second thermal sensor is in thermally conductive contact with a cooling device. A circuit activates the cooling device in order to maintain the second thermal sensor at a temperature that is lower than a temperature of the first thermal sensor. A humidity sensor is in thermally conductive contact with the cooling device. A circuit causes a condensation removal mechanism to be activated for removing liquid from the surface when the humidity sensor indicates a presence of condensation at the temperature that is lower than the temperature of the first thermal sensor.

28 Claims, 7 Drawing Sheets

DEVICES AND METHODS FOR SENSING CONDENSATION CONDITIONS AND FOR REMOVING CONDENSATION FROM SURFACES

TECHNICAL FIELD

The present invention relates to devices and methods for sensing condensation conditions and for removing such condensation from surfaces such as vehicle windscreens, helmet visors, computer monitor screen, windows, electronic equipment, etc., and especially devices and methods that use a thermoelectric cooler (TEC) for automatically and dynamically sensing condensation conditions when condensation appears on a surface or before such condensation actually appears on a surface.

BACKGROUND

The level of moisture in air at any time is commonly referred to as relative humidity. Percent relative humidity is the ratio of the actual partial pressure of steam in the air to the saturation pressure of steam at the same temperature. If the actual partial pressure of steam in the air equals the saturation pressure at any given temperature, the relative humidity is 100 percent. If the actual partial pressure is half that of the saturation pressure, the relative humidity is 50 percent, and so forth.

Dew point temperature, also known as condensation temperature or saturation temperature, is a function of the level of moisture or steam that is present in the air, and is the temperature at which air has a relative humidity of 100 percent. Condensation of moisture on a surface occurs when the temperature of that surface is at or below the dew point temperature of air surrounding the surface.

When air having a relatively high content of moisture comes into contact with a surface having a temperature at or below the dew point temperature, steam will begin to condense out of the air and deposit as water droplets onto the surface. At this time, a thin layer of liquid water comprised of small water droplets forms on the surface, creating a visual hindrance or "fog" to an observer looking at or through the surface. Once, formed, the condensation can be dispersed and removed either by raising the temperature of the surface, thereby changing the water into steam, or by lowering the relative humidity of the air surrounding the surface, thereby allowing the droplets to evaporate.

SUMMARY

The invention provides a device and method for sensing condensation and for removing such condensation from a surface. A first thermal sensor is in thermally conductive contact with the surface. A second thermal sensor is in thermally conductive contact with a cooling device. A circuit activates the cooling device in order to maintain the second thermal sensor at a temperature that is lower than a temperature of the first thermal sensor. A humidity sensor is in thermally conductive contact with the cooling device. A circuit causes a condensation removal mechanism to be activated for removing liquid from the surface when the humidity sensor indicates a presence of condensation at the temperature that is lower than the temperature of the first thermal sensor.

The invention provides a convenient and practical mechanism for detecting condensation conditions quickly, and possibly before they manifest themselves on the surface. In certain embodiments the condensation removal mechanism can be activated automatically when a condensation condition is detected, thereby providing convenience and safety where the surface is a windscreen of a vehicle, for example, or a helmet visor, computer monitor screen, window, electronic equipment enclosure.

Numerous additional features, objects, and advantages of the invention will become apparent from the following detailed description, drawings, and claims.

DESCRIPTION OF DRAWINGS

Like reference symbols in the various drawings indicate like elements.

DETAILED DESCRIPTION

Figure 1:
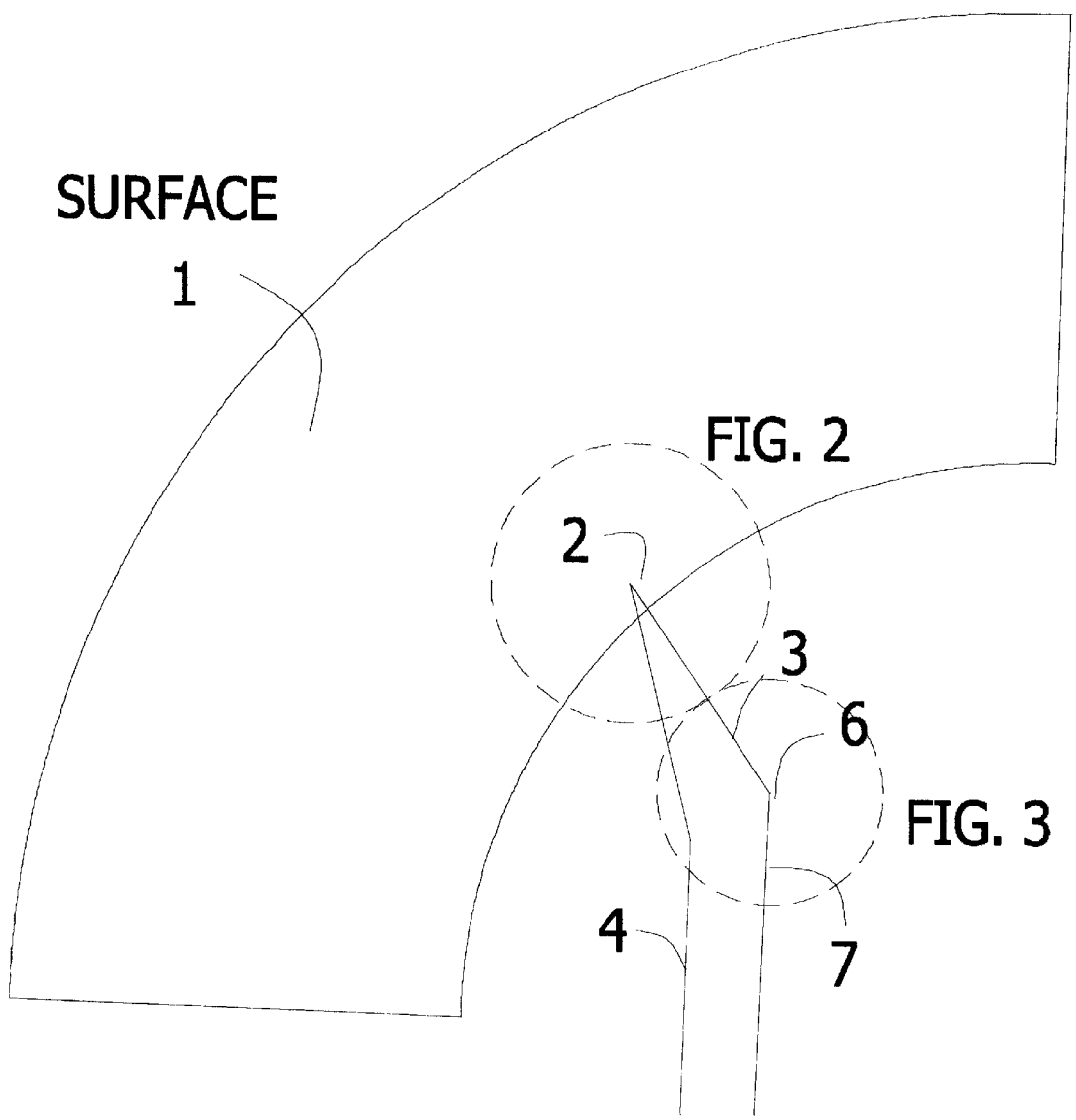
FIG. 1 is a a diagram of a surface in combination with a pair of thermal sensors in accordance with the invention.

With reference to FIG. 1, an automatic sensing and condensation removal system according to the invention includes two thermal sensors 2 and 6. Thermal sensor 2 is mechanically affixed to or embedded within a surface 1 from which liquid is to be removed, such as a windscreen, a visor for a military helmet, pilot helmet, space-suit helmet, or other type of helmet, a computer monitor screen (such as a screen for a commercial electron beam or LCD computer monitor placed outdoors or in a high-humidity environment, such as in an industrial panel), a window or other transparent or translucent pane or enclosure (such as common windows in office buildings or enclosures that may house documents or other sensitive materials such as artwork and artifacts in museums or historic works), including plastics, an electronic equipment enclosure (such as a transparent or non-transparent enclosure for computer equipment, telecommunications equipment, etc. that might be placed outdoors or in high-humidity environments in which condensation might appear on the inside surface of the enclosure).

Each of the thermal sensors is a thermocouple formed by the thermal fusion of two dissimilar but electrically insulated metal conductors. In particular, the thermal fusion of metal conductors 3 and 4 forms thermal sensor 2 and the thermal fusion of metal conductors 3 and 7 forms thermal sensor 6. Conductors 4 and 7 are of the same electro-conductive material and are of the same length.

If the temperatures of the bodies sensed by thermal sensors 2 and 6 are exactly the same, the thermocouple circuit through conductors 4 and 7 creates no electrical current. If the temperatures are not identical, a current is generated through this thermocouple circuit through conductors 4 and 7, this current being proportional to the temperature difference of the two thermocouple junctions, as was first discovered by Thomas Seebeck in 1821.

The integrated sensing and condensation removal device creates an intentional temperature difference between thermocouples 2 and 6 by the thermoelectric cooling effect of a thermoelectric cooler (TEC) onto which thermocouple 6 is mechanically affixed.

Figure 2:
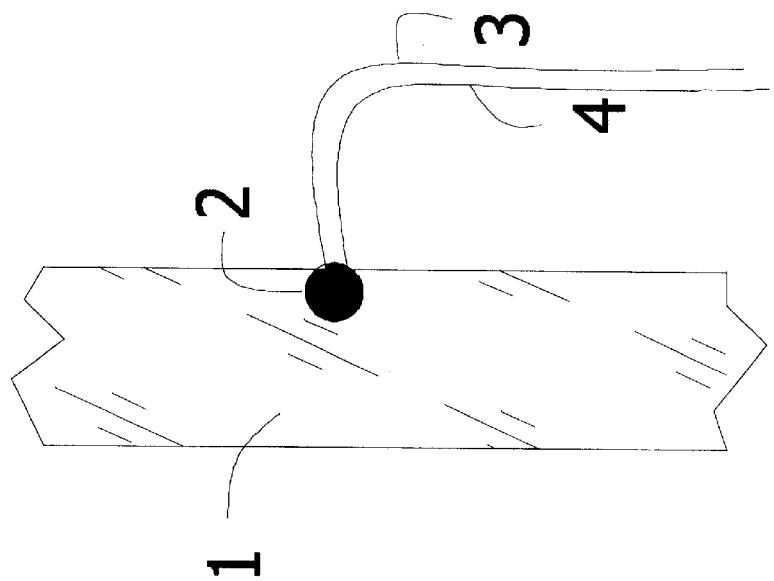
FIG. 2 is a cross-sectional drawing of two options for incorporating a thermal sensor into a surface.
Figure 2:
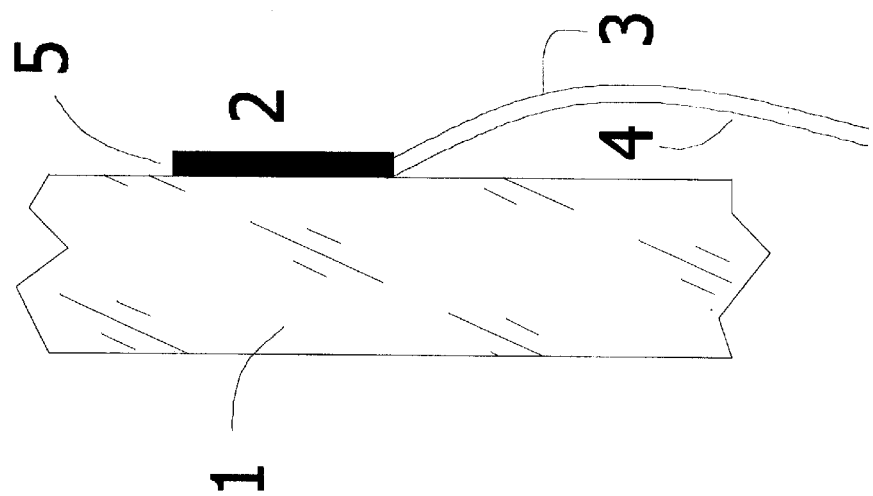

With reference to FIG. 2, thermal sensor 2 may be mechanically affixed to surface 1 by an adhesive 5 (Option 1), or thermal sensor 2 may be embedded within surface 1 (Option 2).

Figure 3:
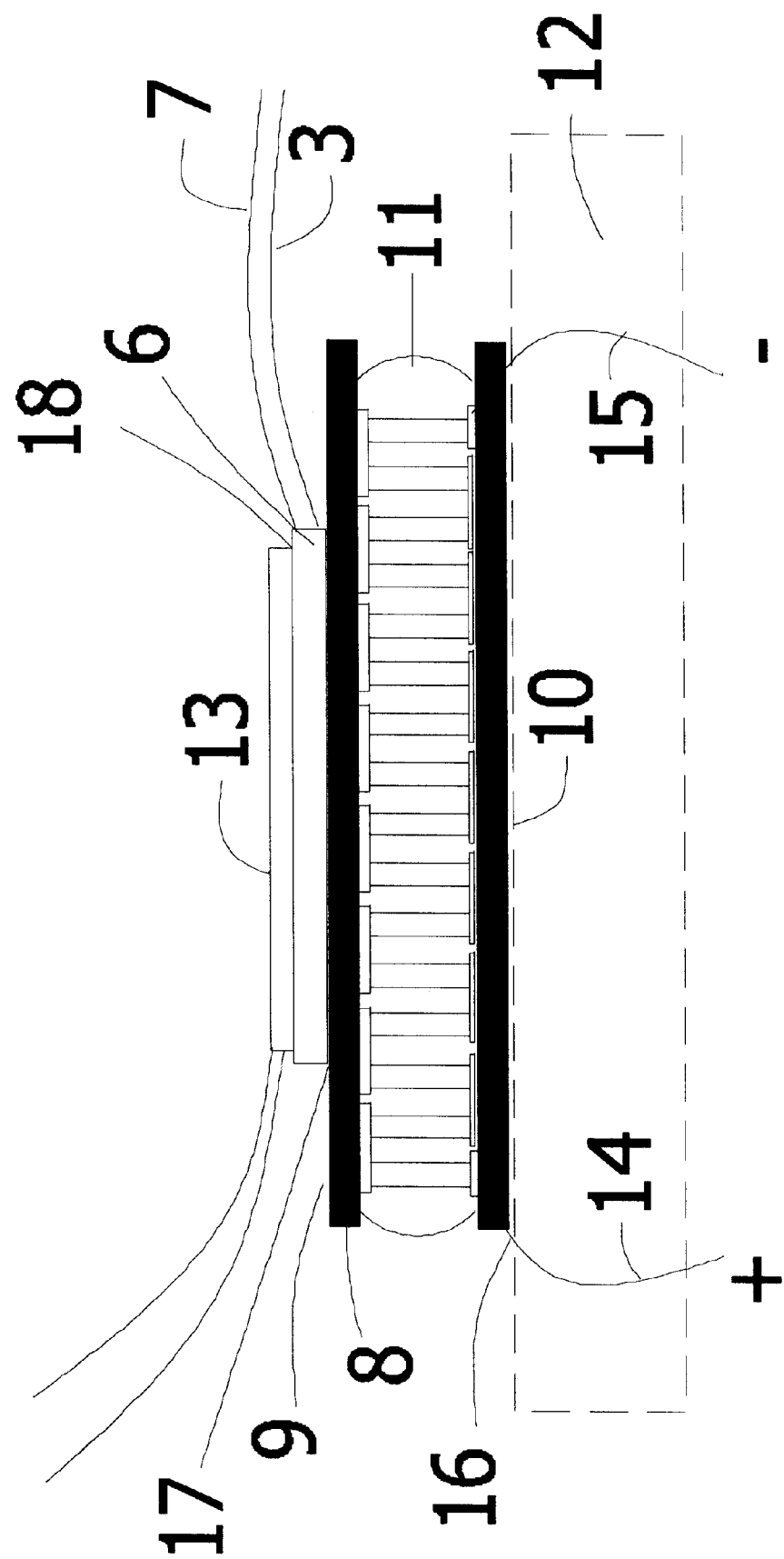
FIG. 3 is a cross-sectional drawing of thermoelectric cooler according to the invention in combination with a thermal sensor.
Figure 6:
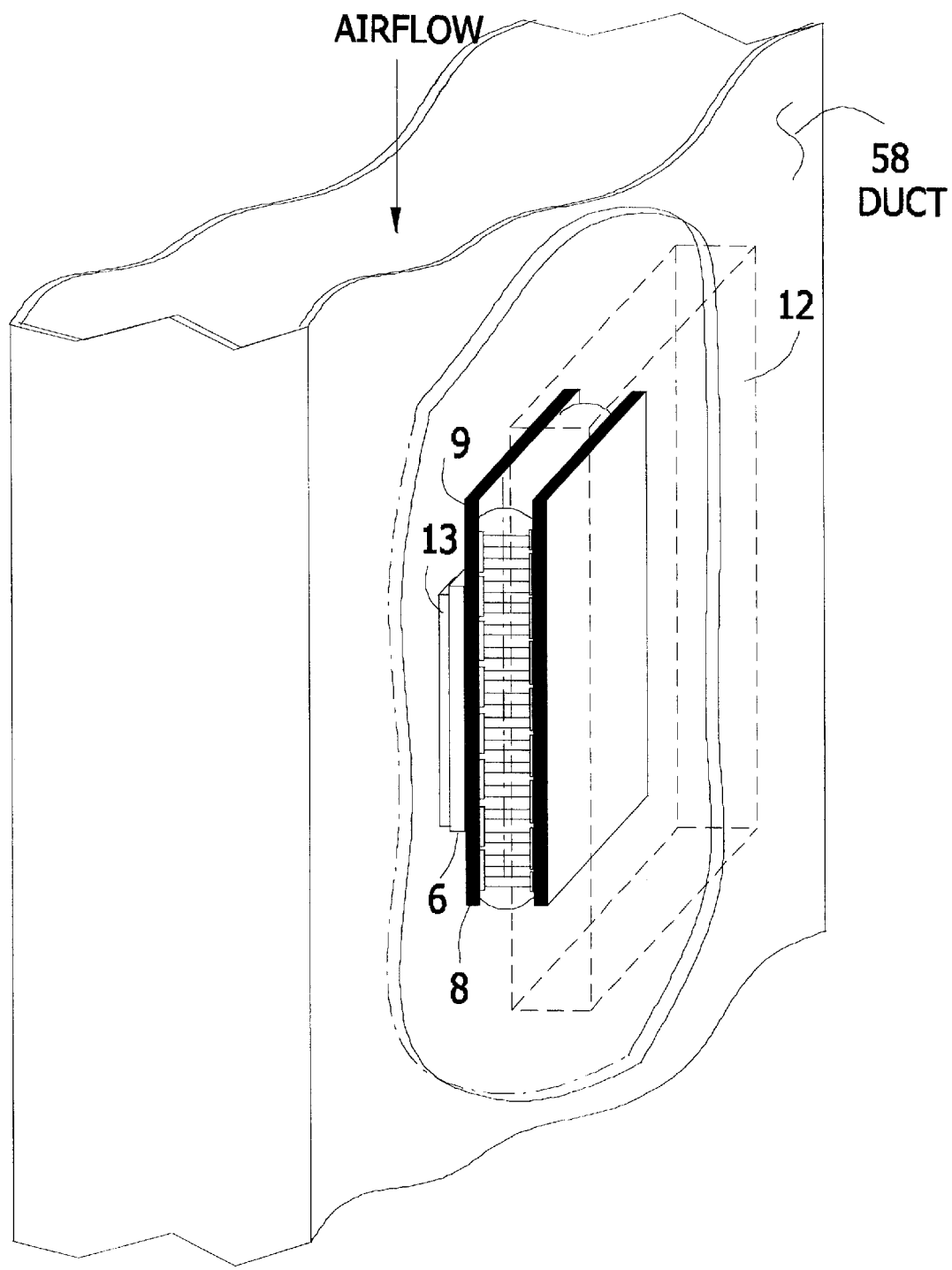
FIG. 6 is a drawing of the thermoelectric cooler and thermal sensor of FIG. 3 within an air duct, the air duct being shown in partial cut-away view.

With reference to FIG. 3, thermal sensor 6 is mechanically affixed by means of an adhesive 17 to the exterior face of the cold junction side 9 of thermoelectric cooler (TEC) 8. The exterior face of the hot side 10 of TEC 8 may be mechanically bonded or otherwise attached to an optional heat sink 12. A thin-layer capacitive sensor 13 is bonded by a mechanical bond 18 to thermocouple 6. Thus, TEC cold-side face 9, thermocouple 6, and capacitive sensor 13 will always be at the same temperature. With reference to FIG. 6, TEC 8, thermal sensor 6, and thin capacitive sensor 13 are placed within the recirculation or outside air duct 58, with heat sink 12 being attached to air duct 58.

Figure 4:
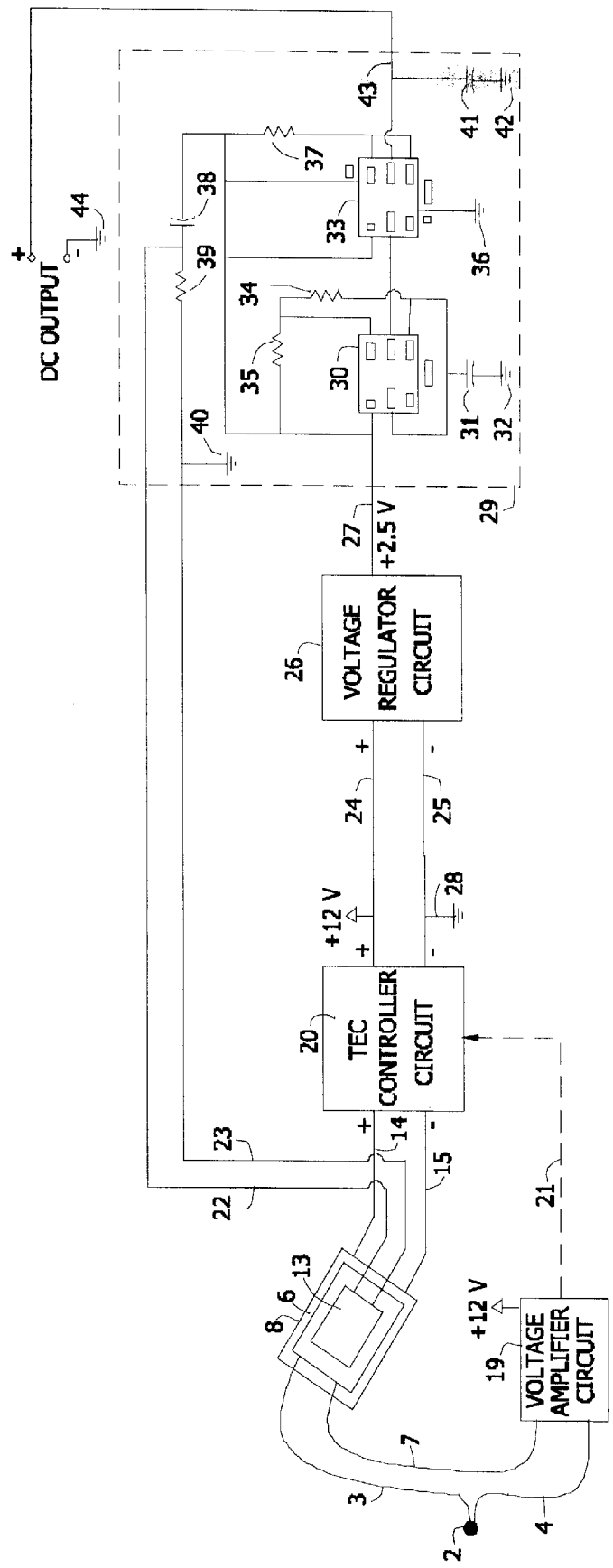
FIG. 4 is a block diagram of the electrical circuitry for an automatic sensing system according to the invention.

With reference to FIG. 4, as the above-mentioned intentionally-created temperature difference is created between thermocouples 2 and 6, and, consequentially, as current is developed within the thermocouple circuit, the resultant voltage difference across conductors 4 and 7 is measured and amplified by voltage amplifier circuit 19. This voltage signal is adjusted and offset for any impressed thermocouple effects due to any dissimilar metal junctions created by the connection of conductors 4 and 7 to voltage amplifier circuit 19 itself. The voltage signal is thereafter fed to TEC controller circuit 20, within which the signal is compared to a pre-established differential voltage set point. Thereafter, TEC controller circuit 20, supplied by a 12-volt power source and electrically grounded at ground 28, electrically modulates a voltage that is applied to TEC 8 by conductors 14 and 15, in order to maintain the cold face of TEC 8 at a temperature level that is a predetermined amount below the temperature of the windscreen, helmet visor, computer monitor screen, window, electronic equipment enclosure, or other surface.

The integrated sensing and condensation removal device is operated in a manner such that a constant difference is dynamically maintained between the temperature established at thermal sensor 6 by the action of TEC 8 and the temperature measured at the surface by thermal sensor 2. Therefore, regardless of the temperature of the surface, the temperature established at the cold-side face of TEC 8 onto which thermal sensor 6 is affixed will always be lower than that of the surface by a predetermined amount.

Ambient air or outside air flows over thin-layer capacitive sensor 13. The capacitance of capacitive sensor 13 will be proportional to the relative humidity of the surrounding air. Because capacitive sensor 13 is maintained at a temperature less than that of the windscreen, helmet visor, computer monitor screen, window, electronic equipment enclosure, or other surface, any liquid condensation will always form on capacitive sensor 13 before it forms on the surface.

Thin-film capacitive sensor 13 is connected by conductors 22 and 23 to capacitance-to-voltage circuit 29. Conductor 23 and capacitance-to-voltage circuit 29 are connected to a common electrical ground 40. Capacitance-to-voltage circuit 29 is supplied regulated 2.5-volt DC power by conductor 27 from voltage regulator circuit 26, which is in turn energized by a 12-volt power source and an electrical ground 28. Capacitance-to-voltage circuit 29 includes two #7556 timing integrated circuits 30 and 33, resistors 34, 35, 37, and 39, and filter capacitors 31, 38, and 41. Timing integrated circuits 30 and 33 are electrically grounded at junctions 32, 36, 42, and 44.

Capacitance-to-voltage circuit 29 transforms the constant 2.5-volt DC supply voltage into a high-frequency AC signal. Thin-film capacitive sensor 13 is integrated into capacitance-to-voltage circuit 29 in a manner such that any capacitance of capacitive sensor 13 is transformed into a positive DC voltage relative to ground 44, at conductor 43 of capacitance-to-voltage circuit 29. The capacitance of capacitive sensor 13 increases as humidity increases, thereby resulting in an increased voltage at conductor 43. The capacitance of capacitive sensor 13 is at a maximum when liquid moisture condenses onto capacitive sensor 13. This condensation of liquid moisture onto capacitive sensor 13, occurs when the temperature of capacitive sensor 13 is at or below the dew point of the ambient air.

Figure 5:
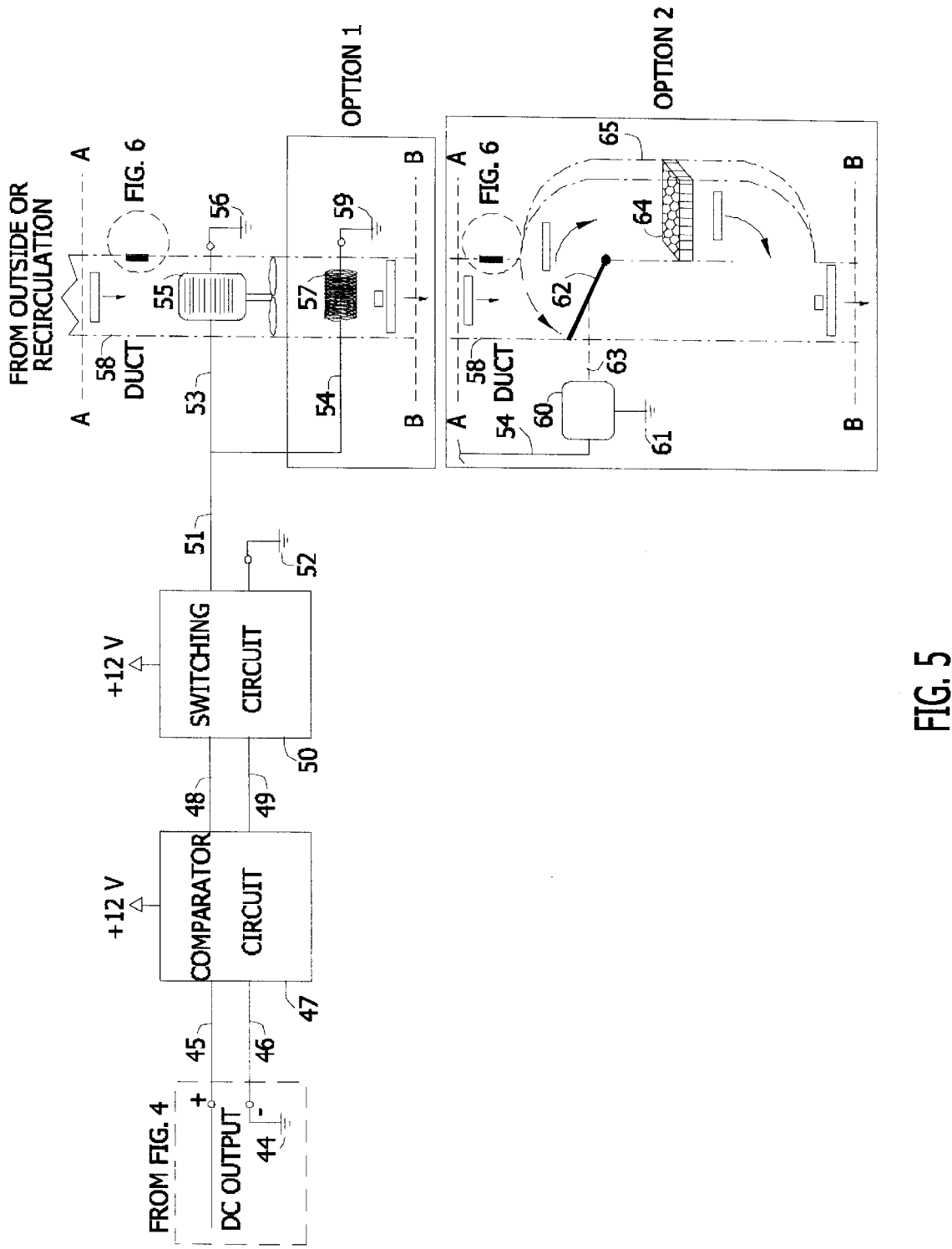
FIG. 5 is a block diagram of the electrical circuitry for two options of a condensation removal system configured to be combined with the automatic sensing system of FIG. 4.

With reference to FIG. 5, the output signal of the capacitance-to-voltage circuit is connected by conductors 45 and 46 to comparator circuit 47. This output signal is compared to a set point voltage previously established in comparator circuit 47. If the signal is less than a pre-established set point, the signal is interpreted as meaning that fogging of the surface is not present or imminent. If the signal is equal to or greater than the pre-established set point, the signal is interpreted as meaning that fogging of the surface is present or imminent, in which case the system activates condensation removal action.

If the signal from the capacitance-to-voltage circuit is equal to or greater than the pre-established set point, a 12-volt signal is directed to switching circuit 50 through conductors 48 and 49, thereby causing the internal electronic or mechanical contactors of switching circuit 50 to close. Thereafter, 12-volt power is directed from switching circuit 50 through conductor 51, which branches into conductors 53 and 54. Conductor 53 is connected to a single-speed or multiple-speed fan 55 located within duct 58. When fan 55 is energized, it rotates or increases its speed in order to generate or increase the volume of airflow directed toward the windscreen, computer monitor screen, window, electronic equipment enclosure, or other surface. The TEC, the thermal sensor mechanically bonded thereto, and the capacitive sensor are positioned within duct 58 upstream of fan 55.

FIG. 5 illustrates a first option (Option 1), according to which 12-volt power is applied by conductor 54 to electrical heating coil 57. Both fan 55 and heating coil 57 are electrically grounded by grounds 56 and 59 respectively. Energization of heating coil 57 raises the temperature of the air flowing over the heating coil element and thereafter flowing to and onto the interior face of the surface, thereby vaporizing water droplets deposited thereon.

According to a second option (Option 2), conductor 12-volt power is applied by conductor 54 to an electric motor or solenoid actuator 60, which is electrically grounded by ground 61. Electric motor or solenoid actuator 60 is connected by linkage arm 63 to damper 62, which moves as indicated in FIG. 5 so as to divert the airstream to an adjacent but interconnecting and parallel duct 65 within which a heater core 64 is mounted. Heater core 64 raises the temperature of the airstream passing through parallel duct 65. Thereafter, the heated air is directed toward and onto the interior face of the surface, thereby vaporizing water droplets deposited thereon.

As a further option, heat from the hot side face of the TEC may be used to provide heat, in lieu of the heating coil 57 or heater core 64, to the air flowing toward and onto the face of the surface, thereby vaporizing water droplets deposited thereon.

As yet a further option, since there will not be any ductwork per se in a helmet, or within certain other equipment having surfaces to be defogged, fan 55, heating coil 57 and heater core 64 may be replaced by a heating coil embedded in or on the visor, etc., as micro-fine electro-resistive wires, or by an infrared source positioned so as to radiate onto the surface.

Figure 7:
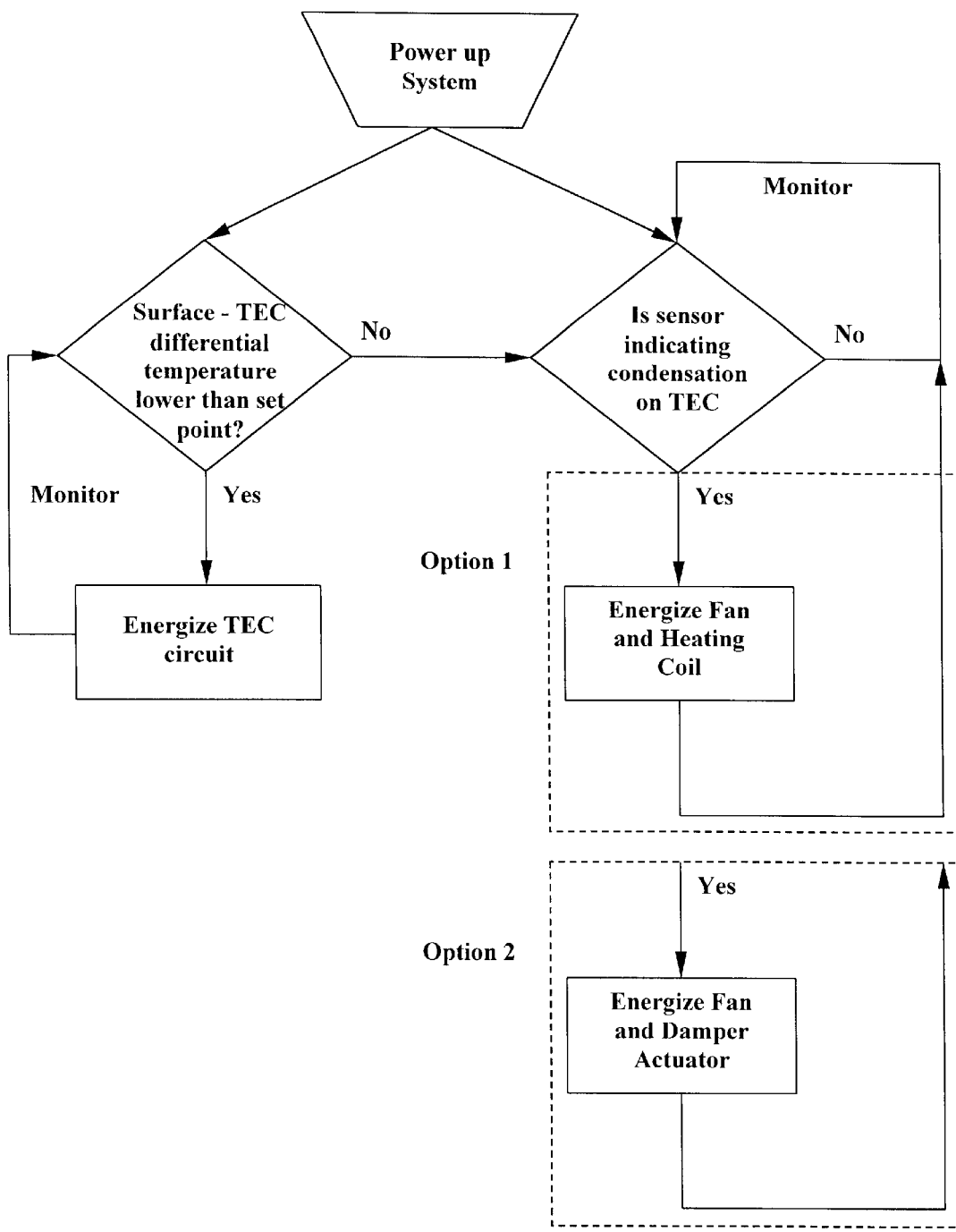
FIG. 7 is a flow diagram of a method for automatically sensing condensation conditions and for removing condensation from surfaces using the system illustrated in FIGS. 1–6.

With reference to FIG. 7, once the automatic sensing and condensation removal system is powered up, the difference in temperature between the windscreen, helmet visor, computer monitor screen, window, electronic equipment enclosure, or other surface and the TEC is monitored to determine whether it is lower than a pre-established set point, and the TEC is energized to the extent necessary to raise the difference to the set point. Also, the capacitive sensor is monitored to determine whether it indicates the presence of condensation. If the capacitive sensor indicates the presence of condensation a fan is energized, and either a heating coil or a damper actuator is activated.

There have been described devices and methods for sensing condensation conditions, and for removing such condensation from surfaces. It will be apparent to those skilled in the art that numerous additions, subtractions, and modifications of the described devices and methods are possible without departing from the spirit and scope of the appended claims. For example, instead of the condensation removal mechanisms being activated directly by the circuitry disclosed herein, the circuitry could provide a warning to a user of a vehicle that includes the windscreen, the helmet that includes the visor, the computer monitor that includes the screen, the room or enclosure that includes the window, the electronic equipment that includes the enclosure, etc., thereby causing the condensation removal mechanism to be activated by the user.

What is claimed is:

1. A device that senses condensation conditions and removes condensation having a given physical state from a surface, comprising:
   a first thermal sensor in thermally conductive contact with the surface;
   a second thermal sensor in thermally conductive contact with a cooling device;
   a circuit configured to activate the cooling device in order to maintain the second thermal sensor at a temperature that is lower than a temperature of the first thermal sensor;
   a humidity sensor in thermally conductive contact with the cooling device;
   a condensation removal mechanism configured to remove condensation having the given physical state from the surface; and
   a circuit configured to cause the condensation removal mechanism to be activated when the humidity sensor indicates a presence of condensation at the temperature that is lower than the temperature of the first thermal sensor.

2. The device of claim 1 wherein the given physical state is a liquid state.

3. The device of claim 1 wherein the surface is a windscreen.

4. The device of claim 3 wherein the surface is a windscreen of a vehicle.

5. The device of claim 1 wherein the surface is a helmet visor.

6. The device of claim 1 wherein the surface is a computer monitor screen.

7. The device of claim 1 wherein the surface is a window.

8. The device of claim 1 wherein the surface is an enclosure for electronic equipment.

9. The device of claim 1 wherein the first and second thermal sensors are thermocouples.

10. The device of claim 1 wherein the first thermal sensor is in actual physical contact with the surface.

11. The device of claim 1 wherein the first thermal sensor is affixed to the surface.

12. The device of claim 1 wherein the first thermal sensor is embedded within the surface.

13. The device of claim 1 wherein the second thermal sensor is in actual physical contact with the cooling device.

14. The device of claim 1 wherein the cooling device is a thermoelectric cooler.

15. The device of claim 1 wherein the humidity sensor is a capacitive sensor.

16. The device of claim 15 wherein the condensation removal mechanism is a hot-side face of the thermoelectric cooler.

17. The device of claim 1 wherein the humidity sensor is in actual physical contact with the second thermal sensor, which is in turn in actual physical contact with the cooling device.

18. The device of claim 1 wherein the condensation removal mechanism comprises a fan.

19. The device of claim 1 wherein the condensation removal mechanism comprises a heating mechanism.

20. The device of claim 1 wherein the condensation removal mechanism comprises a mechanism configured to divert an airstream through a duct having a heating mechanism contained therein.

21. The device of claim 1 wherein the condensation removal mechanism comprises an infrared source.

22. The device of claim 1 wherein the circuit configured to activate the cooling device maintains the second thermal sensor at a temperature that is lower than a temperature of the first thermal sensor by a predetermined amount.

23. The device of claim 1 wherein the circuit configured to cause the condensation removal mechanism to be activated is configured to directly activate the condensation removal mechanism.

24. A method of sensing condensation conditions and removing condensation having a given physical state from a surface having a first thermal sensor in thermally conductive contact therewith, comprising:
   activating a cooling device in order to maintain a second thermal sensor in thermally conductive contact therewith at a temperature that is lower than a temperature of the first thermal sensor; and
   causing a condensation removal mechanism to be activated in order to remove condensation having the given physical state from the surface when a humidity sensor in thermally conductive contact with the cooling device indicates a presence of condensation at the temperature that is lower than the temperature of the first thermal sensor.

25. The method of claim 24 wherein the given physical state is a liquid state.

26. The method of claim 24 wherein the surface is a windscreen.

27. The method of claim 24 wherein the humidity sensor is a capacitive sensor.

28. The method of claim 24 wherein the cooling device maintains the second thermal sensor at a temperature that is lower than a temperature of the first thermal sensor by a predetermined amount.

* * * * *